United States Patent
Blomberg

(10) Patent No.: US 6,718,975 B2
(45) Date of Patent: *Apr. 13, 2004

(54) METHOD OF ASSESSING PULMONARY STRESS AND A BREATHING APPARATUS

(75) Inventor: Urban Blomberg, Solna (SE)

(73) Assignee: Siemens Elema AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/171,340

(22) Filed: Jun. 12, 2002

(65) Prior Publication Data

US 2002/0193699 A1 Dec. 19, 2002

(30) Foreign Application Priority Data

Jun. 19, 2001 (SE) .............................................. 0102221

(51) Int. Cl.⁷ .......................... A61M 16/00; A62B 7/00; F16K 31/02
(52) U.S. Cl. ........................... 128/204.23; 128/202.22; 128/204.21; 128/204.22
(58) Field of Search ....................... 128/200.24, 202.22, 128/204.21, 204.22, 204.23, 204.26

(56) References Cited

U.S. PATENT DOCUMENTS

| 3,621,833 A | * | 11/1971 | Crane .......................... 600/533 |
| 4,267,845 A | * | 5/1981 | Robertson et al. .......... 600/534 |
| 4,351,344 A | | 9/1982 | Stenzler |
| 4,393,869 A | * | 7/1983 | Boyarsky et al. ...... 128/204.18 |
| 5,575,283 A | | 11/1996 | Sjoestrand |
| 5,875,777 A | * | 3/1999 | Eriksson ................. 128/204.21 |
| 5,876,352 A | | 3/1999 | Weismann |
| 6,066,101 A | | 5/2000 | Johnson et al. |
| 6,192,885 B1 | * | 2/2001 | Jalde ...................... 128/205.24 |
| 6,240,920 B1 | * | 6/2001 | Strom .................... 128/204.23 |
| 6,435,182 B1 | * | 8/2002 | Lutchen et al. ........ 128/204.21 |
| 6,510,851 B2 | * | 1/2003 | Rydin et al. ........... 128/204.21 |
| 6,533,730 B2 | * | 3/2003 | Strom ........................ 600/533 |

FOREIGN PATENT DOCUMENTS

| EP | 0 776 672 | 6/1997 |
| EP | 0 904 730 | 3/1999 |
| EP | 1 108 391 | 6/2001 |

* cited by examiner

*Primary Examiner*—Weilun Lo
*Assistant Examiner*—Michael Mendoza
(74) *Attorney, Agent, or Firm*—Schiff Hardin LLP

(57) ABSTRACT

In a method for assessing pulmonary stress, a volume of respiratory gas is received from the lungs of a subject, an ensuing pressure is measured and the pressure-volume (P-V) relationship is analyzed. The analysis includes a determination of the profile of the pressure-volume (P-V) relationship. The profile is straight when no stress is present, convex when there is a risk for over-distension and concave when alveolar units are opened up. Implemented in a breathing apparatus the method can be used to assist an operator in diagnostic and therapeutic considerations in relation to a patient.

15 Claims, 1 Drawing Sheet

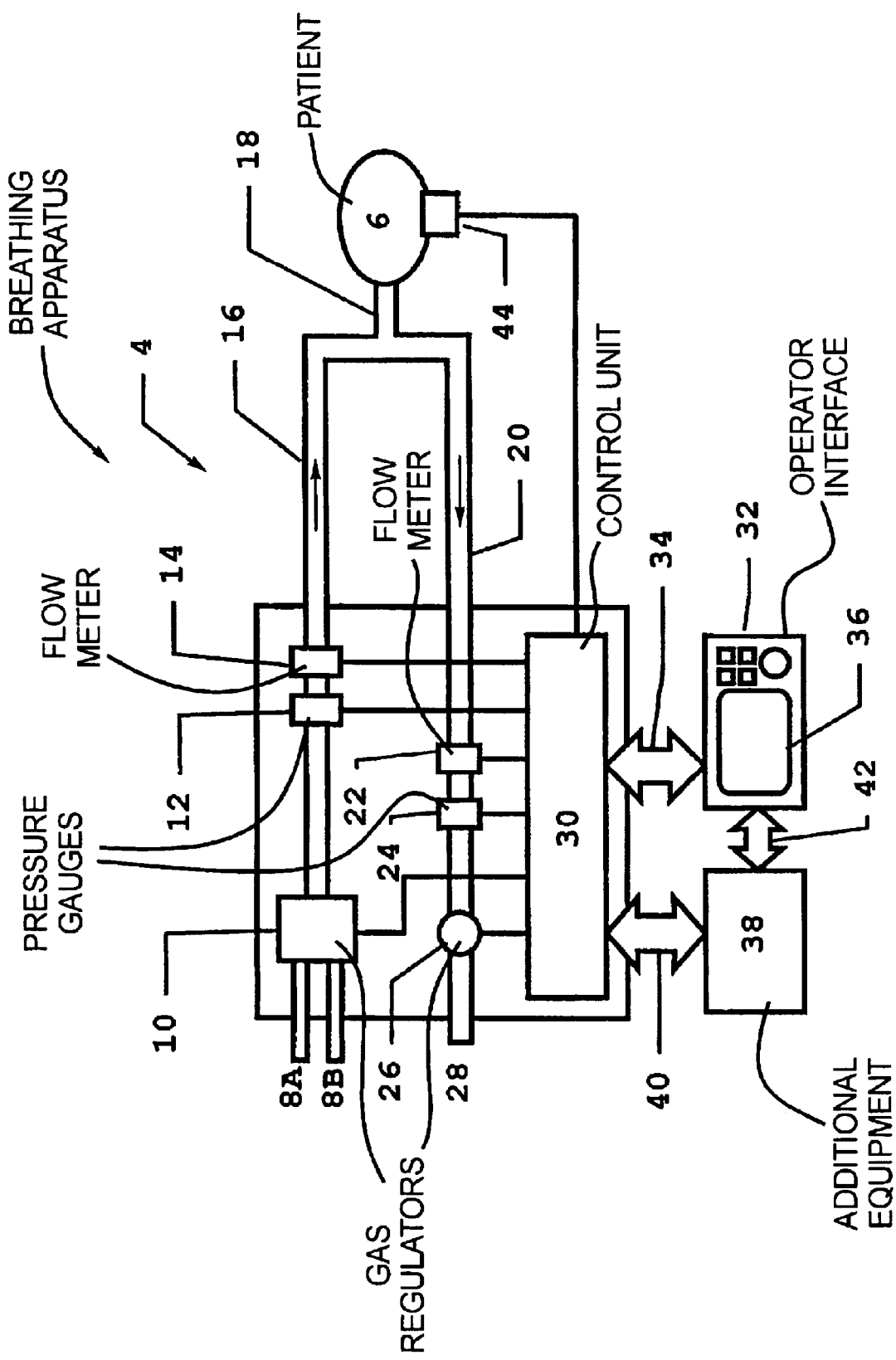

METHOD OF ASSESSING PULMONARY STRESS AND A BREATHING APPARATUS

BACKGROUND OF THE INVENTION

1. Field of the Invention

The present invention relates to a method for determining pulmonary stress, as well as to a breathing apparatus for regulating a respiratory gas flow.

2. Description of the Prior Art

U.S. Pat. No. 4,351,344 discloses a method and apparatus for monitoring lung compliance. A constant flow of gas is supplied during inspiration and a pressure versus time relationship is recorded. The pressure-time relationship is analyzed with respect to linearity. More specifically, the temporal length of a linear slope segment in the pressure-time relationship is determined. The temporal length can be compared with limits and an indication of the compliance status for the patient can be made based on the comparison.

The information thus obtained is, however, insufficient and inconclusive for being properly used in determinations of the status of the lung and as a tool for improving treatment of a lung.

Mechanical ventilation is used as a life saving treatment in many circumstances, but it can aggravate pre-existing disease and even induce lung injury if the dynamics and physiology of mechanical breath delivery are not considered. The lung has an inherent tendency to collapse. During normal breathing this tendency is counteracted by the chest wall and a natural substance called surfactant.

In disease the collapsing tendency becomes more pronounced, giving rise to areas (alveolar units) collapsing early during exhalation/expiration and opening late during inhalation/inspiration. This cyclic opening and closing of airways may initiate lung injury manifest as gross air leaks, diffuse alveolar damage, pulmonary edema and pulmonary inflammation, all of which have been termed Ventilator Induced Lung Injury (VILI). The cyclical opening and closing of alveolar units can be counteracted by the administration of a correctly set Positive End Expiratory Pressure (PEEP).

A second postulated mechanism for VILI is the delivery of large tidal volumes (which can cause volutrauma) or high end inspiratory airway pressure (which can cause barotrauma). Both may over-stretch lung tissues, leading to fluid accumulation, inflammation and increased stiffness of the lung. Baro-volutrauma can be avoided by setting a proper tidal volume or peak pressure.

If the ventilator settings are not optimized, the period before VILI is manifest can be considered as a period of increased stress. Hence, a determination of the degree of lung stress that may follow from a specific ventilator setting can be considered as a pulmonary stress index (PSI).

In previously filed but not published Swedish Patent Application No. 9904643-5 (published on Jun. 20, 2001 as European Application 1 108 391 A2), corresponding to co-pending U.S. application Ser. No. 09/736,346 filed Dec. 15, 2000, a method and apparatus solving these problems is disclosed. The method described in this application is based on P-t measurements made during inspiration.

SUMMARY OF THE INVENTION

It is an object of the invention to provide an alternative method for assessing the pulmonary stress.

This object is achieved in a method that includes obtaining a pressure-volume relationship based on a gas flow received from the lungs of a passively exhaling subject. As disclosed in the previously filed application, this is essentially the same as a P-t relationship since volume is the integral of flow over time. By analyzing the profile of the resulting P-V relationship, essentially the same information can be extracted as in the previously filed Swedish Patent Application mentioned above.

One advantageous analysis is obtained by adapting the profile to a power equation, e.g. in the form of $P=a*V^b+c$, where P is pressure, V is volume and a, b and c are constants. Determination of constant b is particularly interesting since b is a determinant of the shape of the profile. If b equals 1, the profile consists of a straight line, if b is less than 1 the profile is concave and if b is higher than 1 the profile is convex.

Convex profiles have been found to correspond to risks of progressive over-distension of lungs (decreasing compliance) and concave profiles have been found to correspond to risks associated with cyclic closing and opening of alveolar units (increasing compliance). Profiles also can be sigmoidal, i.e. include both concave and convex portions.

Analysis can be performed on pressure-volume relationship on a breath-by-breath basis or on averaged values over a plurality of breaths.

Another advantageous analysis is obtained by adapting the profile to a polynomial equation, or other mathematical expression providing an indicator of convexity or concavity.

The above object also is achieved in a breathing apparatus for implementing the above-described method.

Basically, the apparatus has a gas regulator for regulating respiratory gas flows, a pressure gauge for (directly or indirectly) measuring a pressure, preferably the airway pressure and a control unit for controlling the gas regulator. A meter or unit for determining exhaled volume is also included in the apparatus. The control unit is further adapted to perform the methods described above.

In a preferred embodiment, the control unit is adapted to compare the constant b with an interval, preferably with a lower limit between 0.5 and 0.95 and an upper limit between 1.05 and 1.5. As long as the constant b falls within the interval, there is no pulmonary stress. If the constant b falls outside the interval there is pulmonary stress. The value of the constant b thus provides both an indication of the presence of pulmonary stress and the magnitude of it. The constant b can therefore be used as a value for pulmonary stress index, PSI.

Similar results are obtained when other mathematical expressions are used.

In another preferred embodiment, the apparatus has a display unit and an alarm unit. The control unit is further adapted to perform at least one of a number of actions depending on e.g. the value of the constant b (pulmonary stress index). The control unit can generate an alarm when the stress index is too high or too low, indicating that a possibly injurious therapy is being delivered to a subject. The control unit can display the stress index, as well as the P-V relationship, on the display unit. The control unit can calculate suitable changes in control parameters for reducing pulmonary stress and display these as options for an operator on the display unit. It can automatically re-set the control parameters in accordance with calculations of suitable changes in the control parameters. The control unit can determine if recruiting maneuvers should be provided and can recommend or automatically perform such recruiting maneuvers or actions.

The apparatus according to the invention can advantageously be used for automatic re-setting of PEEP, tidal volume, airway pressure, I:E ratio or other ventilator-controlled parameters.

DESCRIPTION OF THE DRAWINGS

The single FIGURE shows a preferred embodiment of a breathing apparatus constructed and operating according to the invention.

DESCRIPTION OF THE PREFERRED EMBODIMENTS

In the aforementioned co-pending United States application, three different pressure-time diagrams P-t were discussed. The diagrams were obtained by measuring the pressure during constant flow inspiration. The first profile was essentially straight, the second profile was convex and the third profile was concave.

In the present invention and application the same result is obtained by measuring pressure during passive expiration (exhalation). During passive expiration it is only the elastic and resistive properties of the lungs and tubing that affect the pressure. Important here is that the patient does not affect the result by activating respiratory muscles or changing position during expiration. The influence of the tubing can be compensated for when determining the profiles (or when determining the P-t diagram).

The present invention is thus applicable for all situations where gas is passively exhaled by a subject. The manner of supplying the gas is not relevant in the context of the invention. Supply can be made in a controlled mode, where a breathing apparatus or physician exercises full control of supply (whether by pressure control, volume control, etc.). Supply also can be made in a support mode, where the patient can initiate inspiration phases (e.g. volume support, pressure support).

According to the method of the present invention, the helpful information that can be obtained from the convexity or concavity of the P-t expiration profile is essentially the same as described in the aforementioned co-pending United States application, to which reference can be made for further details.

One way of analyzing the expiration P-t profiles is to adapt each profile to a power equation, e.g. $P=a*V^b+c$. P represents airway pressure or $P_{tp}$, but need not necessarily be measured at the airway opening. Pressure can be measured elsewhere and even the pressure drop over a tracheal tube (when used) can be utilized (essentially for compensation calculation or for determining lung pressure). The values a, b and c are constants (for any specific profile). In particular constant b is here of interest, since it is a determinant for the shape of the expiration profile. If b=1, the profile is straight, if b>1, the profile is convex and if b<1, the profile is concave.

It is of course possible to apply other mathematical algorithms for determining the expiration profiles. One simple alternative is to use a polynomial function. Higher orders of polynomial functions also can be used.

Other techniques are also available for use in the analysis. For instance, a straight line can be applied between the first and last co-ordinates of the P-V relationship. If the profile is convex (or essentially convex), most or all co-ordinates will lie below the straight line. If the profile is concave (or essentially concave), most or all co-ordinates will lie above the straight line. A weighting of measured data thus provides the result. Profiles having a sigmoidal shape can be stepwise analyzed and provide an indication of the presence of both convex and concave parts (several values for b). An essentially straight profile will have co-ordinates that are fairly evenly distributed on both sides of the straight line.

The profiles can also be analyzed by using artificial neural networks (ANN), pattern recognition systems, etc.

The following discussion returns to the analysis described initially above, with b-values indicating one of the three profiles.

The convex profile is an indication of a decrease in compliance with increasing tidal volumes. Such decrease is correlated to progressive over-distension. This basically means that the physical limit for expansion of the ventilated alveolar units has been reached. Treatment at this level may not only cause physical injury to lung tissue, but may also have detrimental effects on blood circulation through the lungs.

The concave profile is an indication of an increase in compliance with increasing tidal volumes. Such an increase is correlated to the opening up of alveolar units within the lungs. If a treatment were to display this kind of profile breath after breath (or as an average over a number of breaths), it is a sign of cyclic closing and opening of alveolar units. Such treatment is not ideal and may be injurious to the lungs.

In other words is it beneficial to the patient to arrive at a treatment where the straight profile predominates. This means situations where the constant b=1.

Based on this, the constant b can be used an indication of pulmonary stress. With b as a pulmonary stress index (PSI), the value of the stress index can be used to inform an operator of pulmonary stress. Since there are always variations in the real world, a normal or minimal stress index can be allowed to vary within a predefined interval. The interval could e.g. be 0.9–1.1. The interval can be set by an operator before starting a treatment.

Referring now to the FIGURE which shows a breathing apparatus according to the invention, the breathing apparatus is generally indicated with numeral 4. The apparatus 4 can be connected to a subject, or patient 6. Essentially any animal with lung-dependent respiration can be contemplated as patient.

Gases can enter the apparatus 4 via a first gas inlet 8A and a second gas inlet 8B. The gases are then mixed into a selected respiratory gas in a first gas regulator 10. One gas inlet would be sufficient if the respiratory gas was mixed outside the apparatus 4. More gas inlets can be used where the respiratory gas is to consist of more than two gases. In this embodiment air and oxygen are used as gases.

The gas regulator 10 also regulates pressure and flow of the respiratory gas. The gas regulator 10 normally includes one or more valves for regulating down high-pressure gases, but in portable breathing apparatuses the regulator could also consist of a fan, compressor or similar device for generating a gas flow.

After the gas regulator 10, the respiratory gas passes a first pressure gauge 12 and a first flow meter 14. It then passes through an inspiration line 16 to a patient line 18 and into the patient 6.

From the patient 6 the respiratory gas will flow back through the patient line 18, into an expiration line 20 and via a second flow meter 22, a second pressure gauge 24 and a second gas regulator 26 to a respiratory gas outlet 28. The second gas regulator 26 is normally used to control respiratory gas flow during expiration for upholding a set end pressure (Positive End Expiratory Pressure—PEEP).

The pressure gauges 12, 24 and flow meters 14, 22 need not be located as shown. They can, for instance, be built in within the gas regulators 10, 26. They can also be located elsewhere in the gas flow paths of the apparatus (such as inspiration line 16 and/or patient line 18 and/or expiration line 20). In particular is it possible to locate a pressure gauge within the patient 6 to measure lung or airway pressure. However, based on measurements from pressure gauges 12, 24 and flow meters 14, 22 as shown, corresponding values of e.g. airway pressure can be calculated in known manner.

The operation of the first gas regulator 10 and the second gas regulator 26 is controlled by a control unit 30. The control unit 30 also receives information from the pressure gauges 12, 24 and flow meters 14, 22. Based on the measured information the control unit 30 can, inter alia, determine the above disclosed stress index. The control unit 30 can comprise of any combination of known control components. It could for instance be micro processor based system including one or several processors and memories. Software programming could be used for carrying out the functions. The control unit 30 could also include hardware components such as an EPROM or the like. Other functions and tasks that the control unit 30 can perform are discussed below.

Via an operator interface 32 an operator of the apparatus 4 can communicate with, mainly, the control unit 30 via a first communication link 34. A display 36 can show programmed parameters, selectable functions and parameters as well as diagrams, suggested parameter, parameter waves, the stress index and any conceivable information. The display 36 can be a CRT-screen, a flat screen with or without touch sensitivity, a plasma screen or any suitable screen for displaying images. The display 36 need not be integrated with the operator interface 32 and several displays can be used for one apparatus 4.

Additional equipment (e.g. further displays, PC, Intranet link to databases or remote monitoring stations, Internet link, etc.) is generally indicated with numeral 38 and can be connected to the apparatus 4 for communication. It can be connected to the control unit 30 via a second communication link 40 and/or to the operator interface 32 via a third communication link 42.

The expiration related stress index can be determined during any operational mode of the apparatus 4, in particular all control and support modes. The only requisite is that expiration is passive. Pressure can be measured with pressure gauges 12, 14, which, as mentioned above, can be positioned differently than indicated in the FIGURE. Pressure drop over patient line 18 can also be used.

One example of how the apparatus 4 can be used for a patient 6 will now be described.

Suppose that a patient 6 having partially or completely collapsed lungs is connected to the apparatus 4. Although keeping the patient 6 alive is the primary goal, this should be done with minimum risk of causing further damage to the lungs. The control unit 30 is therefore programmed/constructed to perform a number of actions. These actions can be divided into phases, which can be carried out automatically or after initiative of an operator.

The first phase essentially includes life maintaining measures. The control unit 30 controls the first gas regulator 10 and second gas regulator 26 to provide respiration cycles having an initial tidal volume, an initial respiratory rate, an initial inspiratory time in relation the respiration cycle time, an initial oxygen fraction (FiO2) and an initial PEEP value.

The initial values can be pre-programmed into the control unit 30, but preferably are either entered by the operator via the operator interface 32 or calculated by the control unit 30 based on patient data such as age, weight, diagnosis, or other available information regarding the status of the patient. $FiO_2$ could e.g. initially be set to 100%.

During the respiration cycles the control unit 30 also determines the stress index as described above on a regular basis and compares the stress index with the predefined interval mentioned above. The interval can have a lower limit of ca. 0.6–0.95 and an upper limit of about 1.05–1.4, or any other interval reasonable in view of the initial condition of the patient 6. In the current example with a patient 6 with collapsed lungs, the stress index will most likely fall below the predefined interval.

The second phase is basically meant to start to open the lungs. The control unit 30 will then proceed by (mainly) controlling the second gas regulator 26 to achieve a progressive increase in PEEP. The increase will continue until the stress index exceeds the lower limit, i.e. falls within the predefined interval. The increments by which PEEP is increased can be pre-programmed, calculated by the control unit 30 or entered by the operator.

In the third phase proper opening of the lungs is the aim. To do this one or more recruiting maneuvers are performed by the apparatus 4. A recruiting maneuver essentially consists of a prolonged inspiration (or rather inflation) at an elevated pressure in relation to the initial settings. The inspiration can last up to about a minute and the pressure can be up to 40–60 $cmH_2O$. Again, the values can be higher or lower depending on the specific circumstances. Control parameters for the recruiting maneuver can be pre-programmed, calculated by the control unit 30 or entered by the operator. Other recruiting maneuvers also can be used.

After the recruiting maneuver(s) the stress index is again determined and compared with the predefined interval. Should the stress index be lower or even within the interval (but not optimal), the control unit 30 will control the second gas regulator 26 to increase PEEP again.

Another recruiting maneuver or maneuvers are then supplied, followed by new determination of the stress index.

This procedure of recruiting maneuver(s) and increase of the PEEP value continues until the stress index exceeds the upper limit of the predefined interval. This means that the lung has been fully recruited and can be regarded as fully open.

The fourth phase aims at reaching a proper setting for PEEP. The control unit 30 therefore controls the apparatus 4 to decrease PEEP, while determining the stress index. When the stress index falls within the interval, the settings regarding PEEP thus are essentially optimized.

Since the lungs are open, $FiO_2$ can be lowered. A proper decrease of $FiO_2$ is made when saturation of oxygen is decreased by 1–2%. A meter for saturation and, if required, other patient data is indicated with reference numeral 44 in the FIGURE. The decrease can be performed by the operator or by the control unit 30 (requiring access to saturation measurements).

When the operator wishes to select another respiration mode, the control unit 30 can display the determined "no stress" setting on the display 36 as a suggestion to the operator.

A similar procedure can of course be performed when the profile of the P-V relationship is analyzed in other ways (as described in connection with the method according to the invention). The profile will inevitably exhibit convexity when there is a risk for over-distension and concavity when alveolar units are being opened.

Although not explicitly mentioned above, the breathing apparatus can of course be constructed or adapted to perform or carry out any other function known to persons skilled in the art.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for assessing pulmonary stress, comprising the steps of:

obtaining a volume of expired gas from a passively expiring subject;

measuring pressure in relation to said volume; and assessing pulmonary stress of said subject by determining a profile of said pressure-volume relationship.

2. A method as claimed in claim 1 wherein the step of determining said profile comprises determining a convexity/concavity of said profile.

3. A method as claimed in claim 2 wherein the step of determining said profile comprises adapting said pressure-volume relationship to a power equation $P=a*V^b+c$, wherein P is pressure, V is said volume, and a, b and c are constants, and determining at least the constant b as a determinant for said profile, by determining said profile to be concave if $b<1$ indicative of an increase in lung compliance, determining said profile to be straight if $b=1$ indicative of a constant lung compliance, and determining said profile to be convex if $b>1$ indicating a reduction in lung compliance.

4. A method as claimed in claim 2 wherein the step of determining said profile comprises adapting said pressure-volume relationship to a polynomial equation $P=\alpha+\beta*V+\gamma*V^2$, wherein P is pressure, V is said volume, and $\alpha$, $\beta$ and $\gamma$ are constants, and determining at least the constant $\gamma$ as a determinant for said profile, whereby said profile is concave if $\gamma<0$ indicative of an increase in lung compliance, said profile is straight if $\gamma=0$ indicative of a constant lung compliance, and said profile is convex if $\gamma>0$ indicative of a reduction in lung compliance.

5. A method as claimed in claim 1 comprising determining said profile during each breath of said subject.

6. A method as claimed in claim 1 comprising determining said profile as an average over a plurality of breaths of said subject.

7. A breathing apparatus comprising:

a gas flow path adapted for connection to a respirating, passively expiring subject;

a gas regulator connected to said gas flow path, and a control unit for controlling said gas regulator dependent on at least one set parameter to regulate gas flow in said gas flow path;

a pressure gauge connected to said gas flow path for measuring pressure in said gas flow path;

a volume measuring arrangement connected to said gas flow path for measuring a volume of expired gas from said subject in said gas flow path; and said control unit assessing pulmonary stress of said subject by determining a relationship between said pressure and said volume in said gas flow path, and assessing pulmonary stress of said subject by determining a profile of said pressure-volume relationship, and controlling said gas regulator dependent on said pulmonary stress.

8. A breathing apparatus as claimed in claim 7 wherein said control unit determines a convexity/concavity of said profile.

9. A breathing apparatus as claimed in claim 8 wherein said control unit determines said profile by adapting said pressure-volume relationship to a power equation $P=a*V^b+c$, wherein P is pressure, V is said volume, and a, b and c are constants, by determining at least the constant b as a determinant for said profile, and wherein said control unit determines said profile is concave if $b<1$ indicative of an increase in lung compliance, determines said profile is straight if $b=1$ indicative of a constant lung compliance, and determines said profile is convex if $b>1$ indicative of a reduction in lung compliance.

10. A breathing apparatus as claimed in claim 9 wherein said control unit compares the determined constant b with a predefined interval and analyzes said pulmonary stress as being a minimum if b is within said interval, analyzes an existence of pulmonary stress due to alveolar opening and closing to be present if b is below said predefined interval, and determines alveolar over-distension to be present if b is above said interval.

11. A breathing apparatus as claimed in claim 10 comprising defining said predefined interval for the constant b as having a lower limit between 0.5 and 0.95 and an upper limit between 1.05 and 1.5.

12. A breathing apparatus as claimed in claim 9 wherein said control unit determines said profile by adapting said pressure-volume relationship to a polynomial equation $P=\alpha+\beta*V+\gamma*V^2$, wherein P is pressure, V is said volume, and $\alpha$, $\beta$ and $\gamma$ are constants, and wherein said control unit determines at least the constant $\gamma$ as a determinant for said profile and wherein said control unit compares the determined constant $\gamma$ with a predefined interval and determines a minimum of pulmonary stress to be present if $\gamma$ is within said interval, determines pulmonary stress due to alveolar opening and closing to be present if $\gamma$ is below said interval, and determines alveolar over-distension to be present if $\gamma$ is above said interval.

13. A breathing apparatus as claimed in claim 7 further comprising a display unit and an alarm unit, and wherein said control unit, dependent on the determination of said profile, initiates at least one action selected from the group of actions consisting of generating an alarm via said alarm unit, generating a warning on said display that pulmonary stress is present, determining a change in at least one control parameter for said gas regulator, determining a change in at least one control parameter for said gas regulator and displaying the determined change on said display, determining a change in at least one control parameter for said gas regulator and automatically resetting said at least one control parameter dependent on said change, displaying a recommendation for a recruiting maneuver on said display, and automatically performing a recruiting maneuver.

14. A breathing apparatus as claimed in claim 13 wherein said control parameter is selected from the group consisting of positive end expiratory pressure, fraction of oxygen in said respiratory gas, and tidal volume.

15. A breathing apparatus as claimed in claim 7 wherein said control unit alters said parameter dependent on said pulmonary stress.

* * * * *